United States Patent
Sugiyama et al.

(10) Patent No.: US 11,488,464 B2
(45) Date of Patent: Nov. 1, 2022

(54) DETERMINING NON-TRANSMISSION TIME OF A TERMINAL DEVICE BASED ON A NON-SUPPLY OF POWER

(71) Applicant: NIHON KOHDEN CORPORATION, Tokyo (JP)

(72) Inventors: Takayuki Sugiyama, Tokorozawa (JP); Fumito Horiuchi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 17/204,041

(22) Filed: Mar. 17, 2021

(65) Prior Publication Data

US 2021/0304582 A1    Sep. 30, 2021

(30) Foreign Application Priority Data

Mar. 27, 2020 (JP) .............................. JP2020-058253

(51) Int. Cl.
 *G08B 21/18* (2006.01)
(52) U.S. Cl.
 CPC ................................. *G08B 21/182* (2013.01)
(58) Field of Classification Search
 CPC .......... G08B 21/182; A61B 2560/0204; A61B 2560/0266; A61B 5/0015
 See application file for complete search history.

(56) References Cited

U.S. PATENT DOCUMENTS

2014/0256386 A1*  9/2014  Song ................. H04W 52/0222
                                            455/574
2016/0187949 A1*  6/2016  Sen ................... H04W 52/0277
                                            713/310

FOREIGN PATENT DOCUMENTS

JP         2000-249724 A      9/2000

* cited by examiner

*Primary Examiner* — Hongmin Fan
(74) *Attorney, Agent, or Firm* — Pearne & Gordon, LLP

(57) ABSTRACT

An information generation device includes: a receiver configured to receive physiological information of a subject, from a terminal device configured to operate by power of a battery, and continuously acquire and transmit the physiological information; a determination unit configured to determine whether non-transmission time, during which the terminal device is not capable of transmitting the physiological information to the receiver since the power is not supplied to the terminal device, is equal to or longer than predetermined time; and a generator configured to generate first alert information indicating that the non-transmission time is equal to or longer than the predetermined time, when the determination unit determines that the non-transmission time is equal to or longer than the predetermined time.

8 Claims, 6 Drawing Sheets

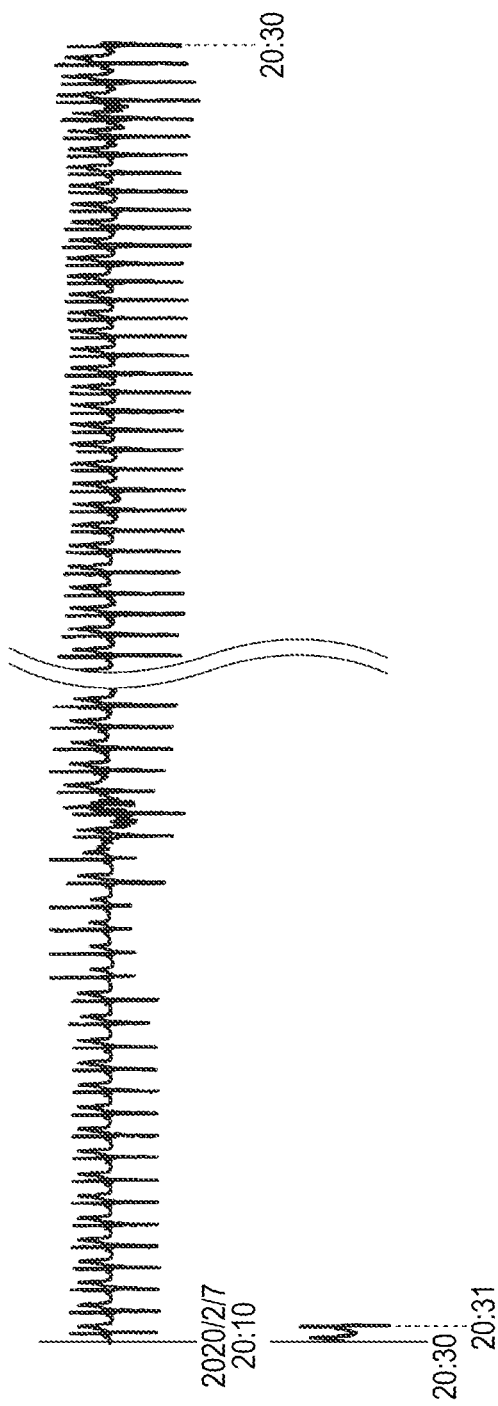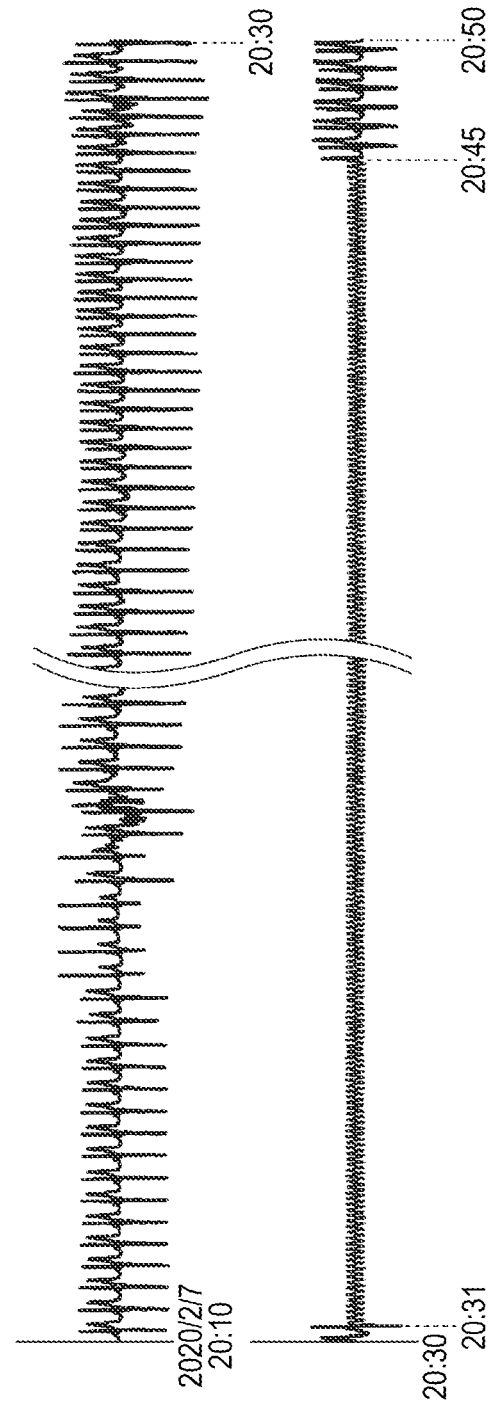
FIG. 4A
FIG. 4B

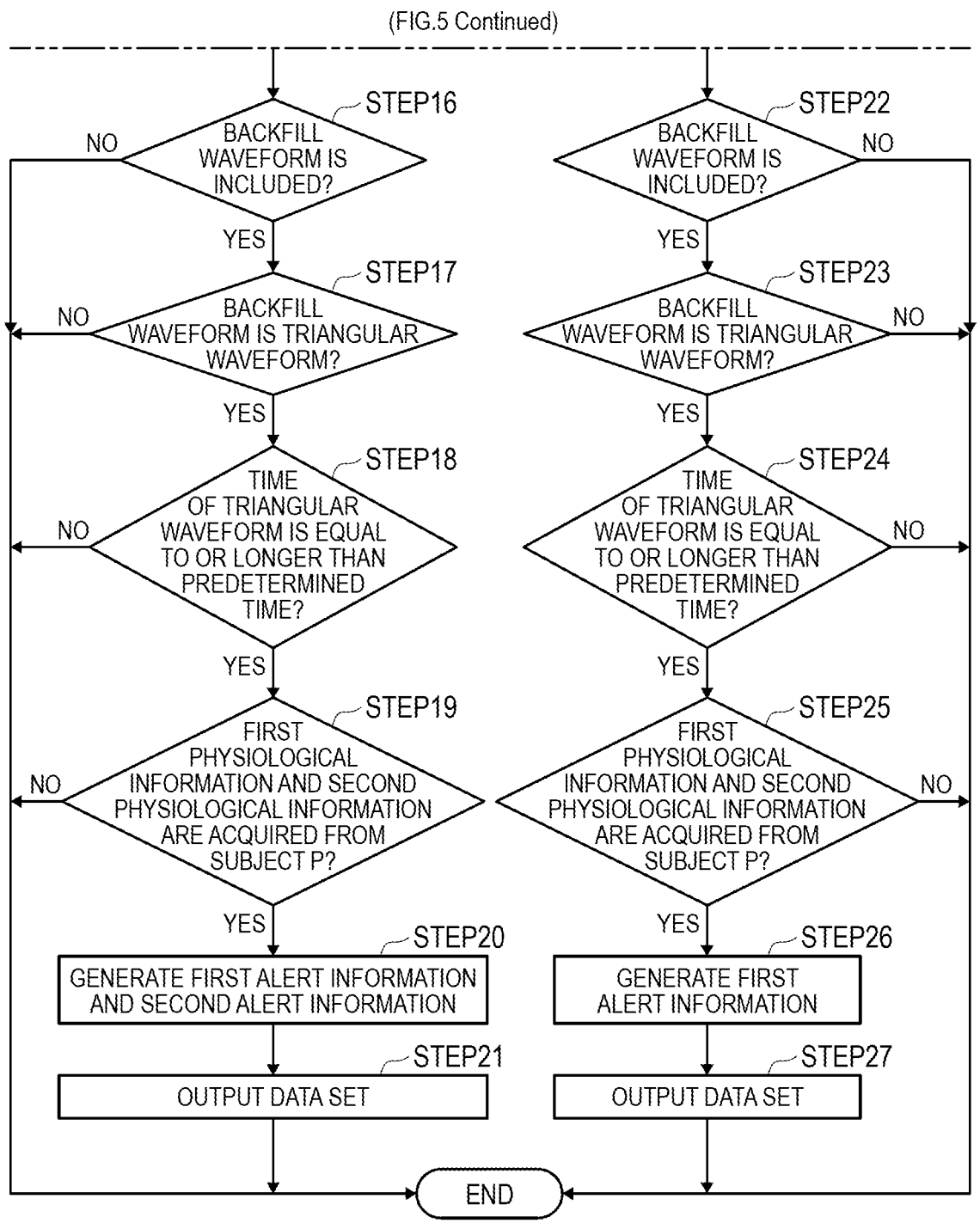

DETERMINING NON-TRANSMISSION TIME OF A TERMINAL DEVICE BASED ON A NON-SUPPLY OF POWER

CROSS-REFERENCE TO RELATED APPLICATIONS

This application is based on and claims priority under 35 USC 119 from Japanese Patent Application No. 2020-058253 filed on Mar. 27, 2020, the contents of which are incorporated herein by reference.

TECHNICAL FIELD

The presently disclosed subject matter relates to an information generation device, an information generation method, and a non-transitory computer-readable medium.

BACKGROUND

A physiological information collection system is known, which includes a terminal device such as a telemeter that operates by battery power, and a receiver that receives information transmitted from the terminal device and displays the information. For example, JP-A-2000-249724 discloses a terminal device in which, when a remaining capacity of a battery provided in the terminal device is less than a predetermined value, a size of an icon of a battery is enlarged and displayed on a screen.

When a battery provided in a terminal device such as a telemeter has run out, an operation of the terminal device stops. Accordingly, it is required to replace the battery as soon as possible.

On the other hand, an emergency situation may suddenly occur before the old battery is removed from the terminal device and a new battery is placed. In this case, time from removing the old battery from the terminal device to placing the new battery may be long.

However, in the past, healthcare professionals have no choice but to actively act with an awareness of inserting a new battery as soon as they remove an old battery from the terminal device. There is room for improvement in this respect.

An object of the presently disclosed subject matter is to provide an information generation device, an information generation method, and a non-transitory computer-readable medium, which can help a healthcare professional appropriately replace a battery provided in a terminal device.

SUMMARY

An information generation device of a first aspect includes: a receiver configured to receive physiological information of a subject, from a terminal device configured to operate by power of a battery, and continuously acquire and transmit the physiological information; a determination unit configured to determine whether non-transmission time, during which the terminal device is not capable of transmitting the physiological information to the receiver since the power is not supplied to the terminal device, is equal to or longer than predetermined time; and a generator configured to generate first alert information indicating that the non-transmission time is equal to or longer than the predetermined time, when the determination unit determines that the non-transmission time is equal to or longer than the predetermined time.

An information generation method of a second aspect includes: receiving physiological information of a subject, from a terminal device configured to operate by power of a battery, and continuously acquire and transmit the physiological information; determining whether non-transmission time, during which the terminal device is not capable of transmitting the physiological information since the power is not supplied to the terminal device, is equal to or longer than predetermined time; and generating first alert information indicating that the non-transmission time is equal to or longer than predetermined time, when it is determined that the non-transmission time is equal to or longer than predetermined time.

A non-transitory computer-readable medium of a third aspect of the presently disclosed subject matter stores a program for causing a computer to execute the information generation method described above.

According to the above configuration, when the determination unit determines that the non-transmission time during which the terminal device cannot transmit the physiological information to the receiver is equal to or longer than the predetermined time, the generator is configured to generate the first alert information indicating that the non-transmission time is equal to or longer than the predetermined time. Therefore, a healthcare professional figures out, for example, the number of times for which the non-transmission time is equal to or longer than the predetermined time by using the first alert information, so that the healthcare professional can know, as numerical data, whether replacement of the battery provided in the terminal device is appropriately performed. As a result, the healthcare professional can aware that the battery provided in the terminal device is appropriately replaced.

In this manner, according to the above configuration, it is possible to help the healthcare professional appropriately replace the battery provided in a terminal device such as a telemeter.

BRIEF DESCRIPTION OF DRAWINGS

FIG. 4A illustrates an example of acquired physiological information;

FIG. 4B illustrates an example of acquired physiological information; and

DESCRIPTION OF EMBODIMENTS

Hereinafter, an example of an embodiment of the presently disclosed subject matter will be described with reference to the drawings.

First Embodiment

Figure 1:
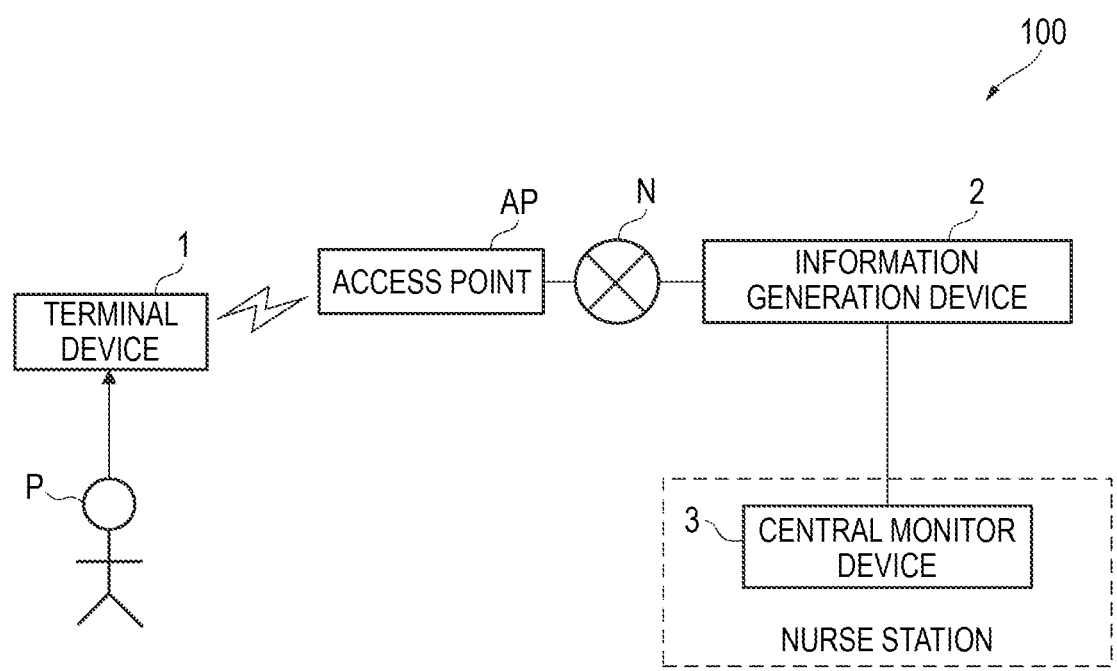
FIG. 1 illustrates a schematic configuration of a medical system according to an embodiment of the presently disclosed subject matter.
Figure 2:
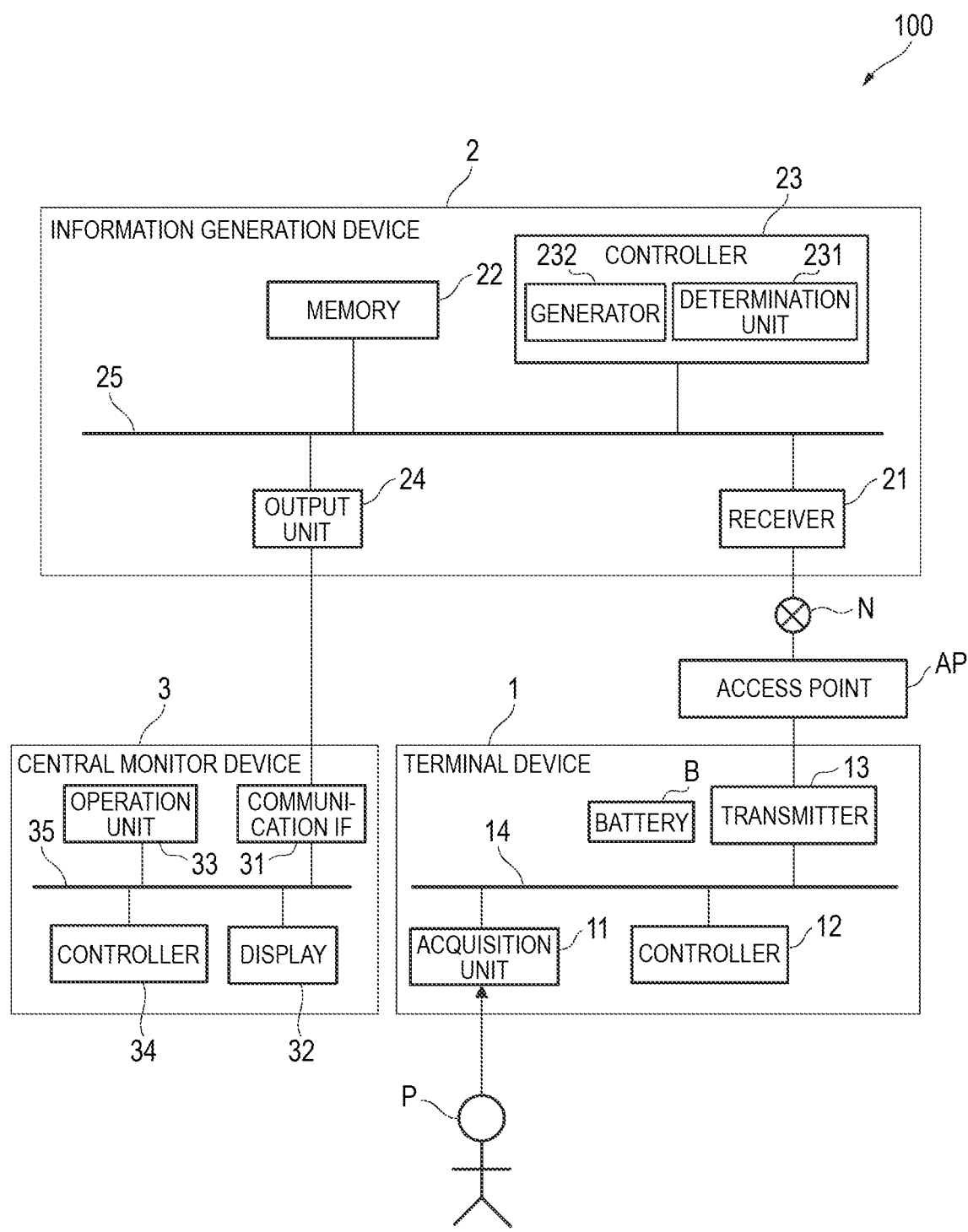
FIG. 2 is a block diagram of the medical system according to the embodiment of the presently disclosed subject matter.

FIG. 1 illustrates a schematic configuration of a medical system 100 according to the present embodiment. FIG. 2 is a block diagram of the medical system 100 according to the present embodiment. The medical system 100 may be applied, for example, in a medical facility such as a hospital. As illustrated in FIG. 1, the medical system 100 includes a terminal device 1, an information generation device 2, and a central monitor device 3. The medical system 100 may include a plurality of terminal devices 1. The terminal device 1 is, for example, a medical telemeter carried by a subject P. The terminal device 1 has a function of communicating with an access point AP, which is installed in various places of a hospital according to a predetermined wireless communication standard, and accessing a network N via the access point AP. The terminal device 1 may communicate with the information generation device 2 by accessing the network N via the access point AP. The information generation device 2 is communicably connected to the central monitor device 3 by wired or wireless communication. The central monitor device 3 is disposed in, for example, a nurse station.

The terminal device 1 includes a removable battery B (see FIG. 2) therein. The terminal device 1 is configured to operate by power supplied from the battery B. Therefore, the terminal device 1 does not operate when the battery B is not provided inside the terminal device 1 or when a remaining capacity of the battery B provided inside the terminal device 1 is 0. In the present embodiment, a state in which the terminal device 1 can operate is referred to as an operable state, and a state in which the terminal device 1 cannot operate is referred to as an inoperable state.

As shown in FIG. 2, the terminal device 1 includes an acquisition unit 11, a controller 12, and a transmitter 13. The acquisition unit 11, the controller 12, and the transmitter 13 are communicably connected to one another via a bus 14. When the terminal device 1 is in an operable state, the acquisition unit 11 is configured to acquire authentic physiological information of the subject P. The authentic physiological information refers to physiological information acquired from the subject P. The authentic physiological information refers to physiological waveform data related to, for example, electrocardiogram, pulse, electroencephalogram, non-invasive arterial oxygen saturation ($SpO_2$), body temperature, blood pressure, and respiratory rate. The acquisition unit 11 transmits the acquired authentic physiological information to the transmitter 13 based on a control signal from the controller 12.

The controller 12 includes one or more memories and one or more processors as hardware configurations. The memory is configured with, for example, a read-only memory (ROM) in which various programs and the like are stored, or a random access memory (RAM) including a plurality of work areas in which various programs executed by the processor and the like are stored. The processor is, for example, a central processing unit (CPU), and is configured to load a program specified from various programs incorporated in the ROM onto the RAM and execute various types of processing in cooperation with the RAM. The controller 12 performs control such that processing of the acquisition unit 11 or the transmitter 13 is implemented by, for example, executing the program by the processor of the controller 12 in cooperation with the RAM.

The controller 12 is configured to monitor a remaining capacity of the battery B provided in the terminal device 1. When the remaining capacity of the battery B provided in the terminal device 1 is equal to or less than a predetermined value, the controller 12 generates battery depletion advanced notification information (an example of information on the remaining capacity of the battery B) indicating that the remaining capacity of the battery B is equal to or less than the predetermined value. The predetermined value of the remaining capacity of the battery B is, for example, 15%. When the remaining capacity of the battery B provided in the terminal device 1 is equal to or less than a predetermined value, the controller 12 may be configured to determine a time point at which the remaining capacity of the battery B is 0 (hereinafter, referred to as battery depletion time point) based on a remaining capacity of the battery B and power consumption per minute of the battery B. In this case, the controller 12 generates battery depletion time point information (an example of information on the remaining capacity of the battery B) based on the determination result.

When the battery B whose remaining capacity is not 0 is provided in the terminal device 1, the controller 12 is also configured to monitor a communication state between the terminal device 1 and the access point AP. The communication state between the terminal device 1 and the access point AP is a connected state or an unconnected state. The connected state refers to a state in which the terminal device 1 is in the operable state and is connected to the access point AP. On the other hand, the unconnected state refers to a state in which the terminal device 1 is not connected to the access point AP due to radio wave disconnection although the terminal device 1 is in the operable state. Even when the communication state between the terminal device 1 and the access point AP is in the unconnected state, the acquisition unit 11 may acquire the authentic physiological information from the subject P.

The controller 12 may control the transmitter 13 to transmit various pieces of information, such as the authentic physiological information and the information on the remaining capacity of the battery B, to the information generation device 2. When the acquisition unit 11 acquires the authentic physiological information and the communication state between the terminal device 1 and the access point AP is a connected state, the controller 12 controls the transmitter 13 to continuously transmit the authentic physiological information to the information generation device 2 via the access point AP and the network N. In this case, the authentic physiological information is transmitted to the information generation device 2 as soon as the authentic physiological information is acquired. On the other hand, when time (non-transmission time) exists, at which the terminal device 1 cannot transmit the authentic physiological information to the information generation device 2 since the terminal device 1 is in the inoperable state or the communication state between the terminal device 1 and the access point AP is an unconnected state, the controller 12 controls the transmitter 13 to transmit complementary physiological information corresponding to the non-transmission time at a time point at which the terminal device 1 is in an operable state and the communication state between the terminal device 1 and the access point AP is a connected state. In the present embodiment, a physiological waveform corresponding to complementary physiological information is referred to as backfill waveform. In the present embodiment, a function of transmitting complementary physiological information from the terminal device 1 to the information generation device 2 when the terminal device 1 is in an operable state and the communication state between the terminal device 1 and the access point AP is a connected state is referred to as backfill function.

The complementary physiological information is authentic physiological information that is acquired when the communication state between the terminal device 1 and the access point AP is an unconnected state, or pseudo physiological information. The pseudo physiological information refers to, for example, physiological information indicating that the authentic physiological information cannot be acquired from the subject P since the terminal device 1 is in an inoperable state. In the present embodiment, the pseudo physiological information is data of a waveform having a triangular shape. For example, complementary physiological information in a case where the transmitter 13 cannot transmit the authentic physiological information to the information generation device 2 since the communication state between the terminal device 1 and the access point AP is an unconnected state is the authentic physiological information acquired when the communication state between the terminal device 1 and the access point AP is the unconnected state. On the other hand, complementary physiological information in a case where the transmitter 13 cannot transmit the authentic physiological information to the information generation device 2 since the terminal device 1 is in an inoperable state is the pseudo physiological information. In the present embodiment, the phrase "physiological information" can be used as an expression that includes the authentic physiological information and the pseudo physiological information.

The transmitter 13 is configured to transmit, based on the control signal from the controller 12, the physiological information or the information on the remaining capacity of the battery B to the information generation device 2 via the access point AP and the network N by a communication method such as Wi-Fi.

When transmitting the physiological information to the information generation device 2, the transmitter 13 may transmit other information different from the physiological information together with the physiological information based on the control signal from the controller 12. The transmitter 13 may also transmit, together with the physiological information, for example, identification information of the terminal device 1, information on a subject associated with the terminal device 1, information on a healthcare professional responsible for the subject, information on a ward to which the subject belongs, and information on an acquisition time point of the physiological information acquired by the acquisition unit 11.

The information generation device 2 includes a receiver 21, a memory 22, a controller 23, and an output unit 24. The receiver 21, the memory 22, the controller 23, and the output unit 24 are communicably connected to one another via a bus 25. The receiver 21 is configured to continuously receive the physiological information transmitted from the terminal device 1 via the access point AP and the network N. The receiver 21 transmits the received physiological information to the memory 22.

The memory 22 stores the physiological information of the subject P, table information for associating the identification information of the terminal device 1 with the subject P or the healthcare professional, table information for associating the subject P or the healthcare professional with the ward, information on the acquisition time point of the physiological information, and the like.

The controller 23 may have, for example, a hardware configuration similar to that of the controller 12. The controller 23 includes a determination unit 231 and a generator 232. The controller 23 performs control such that processing of the determination unit 231 or the generator 232 is implemented by, for example, executing a program by a processor of the controller 23 in cooperation with the RAM. The controller 23 may specify the subject P associated with the identification information of the terminal device 1, the healthcare professional responsible for the subject P, the ward to which the subject belongs, and the like, based on, for example, the identification information of the terminal device 1 received from the terminal device 1 and various pieces of table information stored in the memory 22. The controller 23 may also control the memory 22 and the output unit 24.

Here, the program executed by the processor of the controller 23 may be stored by using various types of non-transitory computer-readable media, and can be supplied to a computer. The non-transitory computer-readable media include various types of tangible storage media. Examples of the non-transitory computer-readable media include magnetic recording media (for example, flexible disks, magnetic tapes, and hard disk drives), magneto-optical recording media (for example, magneto-optical disks), read only memories (CD-ROM), CD-R, CD-R/W, and semiconductor memories (for example, mask ROMs, programmable ROMs (PROM), erasable PROMs (EPROMs), and flash ROMs).

The determination unit 231 may determine whether the complementary physiological information is the authentic physiological information or the pseudo physiological information based on features of a shape of a waveform corresponding to the complementary physiological information. The determination unit 231 determines whether the complementary physiological information is the authentic physiological information or the pseudo physiological information based on, for example, whether a physiological waveform (backfill waveform) corresponding to the complementary physiological information is a triangular waveform. When determining that the complementary physiological information is the authentic physiological information, the determination unit 231 determines that non-transmission time is generated because the communication state between the terminal device 1 and the access point AP is an unconnected state. On the other hand, when determining that the complementary physiological information is the pseudo physiological information, the determination unit 231 determines that the non-transmission time is generated because power is not supplied to the terminal device 1 and the terminal device 1 is in an inoperable state.

When determining that the complementary physiological information is the pseudo physiological information, the determination unit 231 determines whether the non-transmission time is equal to or longer than predetermined time based on a length of the non-transmission time (that is, a difference between a time point at which the terminal device 1 transmits the complementary physiological information to the information generation device 2 and a time point at which the terminal device 1 cannot transmit the authentic physiological information to the information generation device 2). When the non-transmission time is equal to or longer than the predetermined time, the determination unit 231 generates first determination information. The first determination information refers to information indicating that non-transmission time generated since power is not supplied to the terminal device 1 is equal to or longer than the predetermined time. The predetermined time may be optionally set by a healthcare professional or the like.

The determination unit 231 may also determine whether physiological information acquired immediately before the non-transmission time (hereinafter, referred to as first physiological information) and physiological information acquired immediately after the non-transmission time (hereinafter, referred to as second physiological information) is physiological information on the same subject. The determination unit 231 determines whether the first physiological information and the second physiological information is acquired from the same subject by, for example, pattern-matching a waveform corresponding to the first physiological information and a waveform corresponding to the second physiological information.

The determination unit 231 may determine the battery depletion time point of the battery B provided in the terminal device 1 based on the battery depletion advanced notification information received from the terminal device 1. The determination unit 231 determines the battery depletion time point based on, for example, the battery depletion advanced notification information and the power consumption per minute of the battery B.

The determination unit 231 may determine whether the receiver 21 receives the physiological information from the terminal device 1 within the predetermined time from the battery depletion time point. When determining that the physiological information is not received from the terminal device 1 within the predetermined time from the battery depletion time point, the determination unit 231 generates second determination information indicating that the receiver 21 does not receive the physiological information from the terminal device 1 within the predetermined time from the battery depletion time point. Namely, the determination unit 231 generates the second determination information when a time point at which the receiver 21 receives the physiological information from the terminal device 1 after the time point at which the remaining capacity of the battery B is 0 is a time point that has elapsed from the battery depletion time point by the predetermined time. The predetermined time may be optionally set by a healthcare professional or the like.

The generator 232 is configured to generate first alert information based on the first determination information. The first alert information refers to information for presenting to the healthcare professional or the like that the non-transmission time generated since power is not supplied to the terminal device 1 is equal to or longer than the predetermined time. The first alert information is transmitted to the memory 22.

The generator 232 is configured to generate second alert information based on the second determination information. The second alert information refers to information for presenting to the healthcare professional or the like that the receiver 21 does not receive the physiological information from the terminal device 1 within the predetermined time from the battery depletion time point. The second alert information is transmitted to the memory 22.

The generator 232 may also generate information on a time point at which the first alert information is generated, or the like.

The controller 23 associate information on the subject, which is specified by the controller 23 or is received from the terminal device 1, or information on a time point, at which the first alert information or the first alert information and the second alert information generated by the generator 232 is generated, with the first alert information or the first alert information and the second alert information. In this case, the associated information is transmitted to the memory 22.

The output unit 24 receives, based on a control signal from the controller 23, a data set, which includes the first alert information or the first alert information and the second alert information in a predetermined period, and at least one of information on the subject P, information on the healthcare professional, information on the ward, and information on the time point at which the first alert information is generated, which is in the predetermined period, from the memory 22. For example, when the healthcare professional performs, on an operation unit 33 provided in the central monitor device 3 described below, an operation for outputting a data set for the last five days, a command signal for outputting the data set in the period is transmitted to the controller 23 of the information generation device 2 from the central monitor device 3. The controller 23 controls the output unit 24 to output the data set in the period based on the command signal and output an output signal OS corresponding to the output data set to the central monitor device 3. The predetermined period may be optionally set by a healthcare professional or the like.

The central monitor device 3 includes a communication interface (hereinafter, referred to as a communication IF) 31, a display 32, the operation unit 33, and a controller 34. The communication IF 31, the display 32, the operation unit 33, and the controller 34 are communicably connected to one another via a bus 35. The communication IF 31 is an interface that enables connection to the information generation device 2. The central monitor device 3 may appropriately communicate with the information generation device 2 via the communication IF 31.

The display 32 is, for example, a display device such as a liquid crystal display and an organic EL display. The display 32 displays various pieces of information such as the first alert information and the second alert information.

The operation unit 33 is configured to accept an input operation of an operator to operate the central monitor device 3, and generate an instruction signal corresponding to the input operation. The operation unit 33 is, for example, a touch panel overlaid on the display 32, or an operation button attached to a housing of the central monitor device 3. The operation unit 33 accepts an input operation for displaying predetermined information on the display 32, or an input operation for giving a predetermined instruction to the output unit 24 of the information generation device 2, and generates an instruction signal corresponding to the input operation. The generated instruction signal is transmitted to the controller 34 via the bus 35. For example, when an instruction signal corresponding to the input operation for giving the predetermined instruction to the output unit 24 of the information generation device 2 is transmitted to the controller 34, the controller 34 transmits the instruction signal to the information generation device 2.

The controller 34 may have, for example, a hardware configuration similar to that of the controller 12. The controller 34 may control the communication IF 31, the display 32, and the operation unit 33.

First Embodiment

Figure 3:
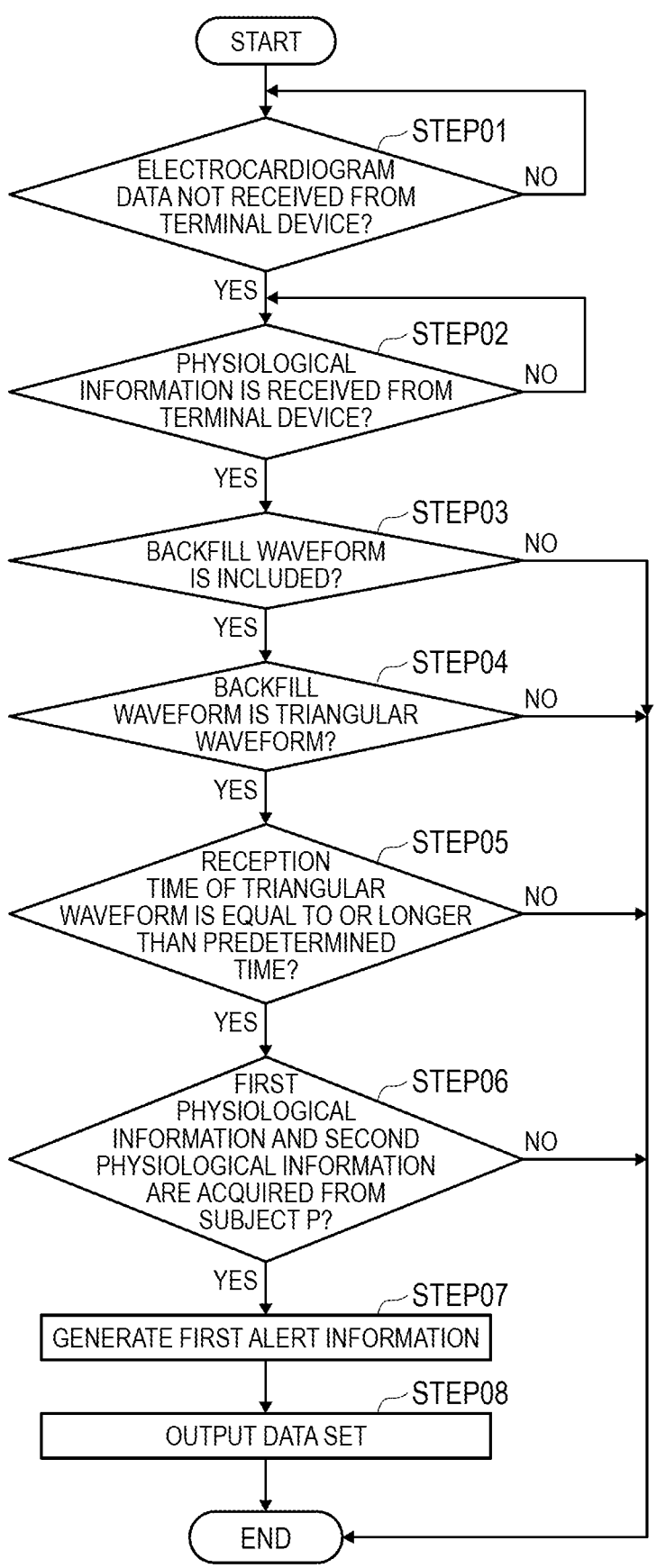
FIG. 3 is a flowchart according to a first embodiment.

Next, a flow until the data set is output in the first embodiment is illustrated with reference to FIGS. 3 and 4. FIG. 3 is a flowchart according to the first embodiment. FIGS. 4A and 4B illustrate an example of the acquired physiological information. FIGS. 4A and 4B illustrate physiological information of the subject P, which is acquired from 20:10 to 20:50 on Feb. 7, 2020. In the present embodiment, authentic physiological information acquired from the subject P is electrocardiogram data. In the present embodiment, when non-transmission time of physiological information transmitted to the information generation device 2 from the terminal device 1 is 10 minutes or longer, the determination unit 231 determines that the battery B is not replaced appropriately.

As illustrated in FIG. 3, when the terminal device 1 starts to acquire electrocardiogram data from the subject P, the controller 23 of the information generation device 2 determines whether the electrocardiogram data of the subject P is not received from the terminal device 1 (STEP01). When the receiver 21 receives the electrocardiogram data of the subject P from the terminal device 1 (NO in STEP01), STEP01 is repeated. On the other hand, when the receiver 21 does not receive the electrocardiogram data of the subject P from the terminal device 1 (YES in STEP01), the processing proceeds to STEP02.

As illustrated in FIG. 4A, in the present embodiment, the receiver 21 receives electrocardiogram data from the terminal device 1 from 20:10 to 20:31, but the receiver 21 does not receive electrocardiogram data from the terminal device 1 after 20:31. Therefore, the controller 23 repeats STEP01 from 20:10 to 20:31, and at the time point of 20:32, the controller 23 determines that the receiver 21 does not receive the electrocardiogram data of the subject P from the terminal device 1 (YES in STEP01), and starts processing of STEP02.

In STEP02 of FIG. 3, the controller 23 determines whether the receiver 21 receives physiological information from the terminal device 1. When the receiver 21 does not receive the physiological information from the terminal device 1 (NO in STEP02), the STEP02 is repeated. On the other hand, when the receiver 21 receives the physiological information from the terminal device 1 (YES in STEP02), the processing proceeds to STEP03.

As illustrated in FIG. 4B, in the present embodiment, the receiver 21 receives the physiological information from the terminal device 1 at a time point of 20:45 after the electrocardiogram data is not received from the terminal device 1. Therefore, at 20:45, the controller 23 determines that the receiver 21 receives the physiological information from the terminal device 1, and the controller 23 starts processing of STEP03. In this case, the electrocardiogram data acquired immediately before the non-transmission time (from 20:32 to 20:44), that is, before 20:31 corresponds to the first physiological information. The physiological information acquired immediately after the non-transmission time (from 20:32 to 20:44), that is, after 20:45 corresponds to the second physiological information.

In STEP03 of FIG. 3, the controller 23 determines whether the physiological information received in STEP02 includes a backfill waveform. When the physiological information received in STEP02 does not include the backfill waveform (NO in STEP03), the controller 23 ends the present processing. On the other hand, when the physiological information received in STEP02 includes the backfill waveform (YES in STEP03), the processing proceeds to STEP04.

As illustrated in FIG. 4B, in the present embodiment, the time from 20:32 to 20:44 is the non-transmission time. The receiver 21 receives, at 20:45, complementary physiological information corresponding to the non-transmission time, and electrocardiogram data at 20:45 from the terminal device 1. Therefore, the controller 23 determines that the physiological information received in STEP02 includes the backfill waveform (YES in STEP03), and starts processing of STEP04. When the terminal device 1 does not have the backfill function, the terminal device 1 cannot transmit the complementary physiological information corresponding to the non-transmission time to the information generation device 2. In this case, the receiver 21 receives, at the time point of 20:45, only the electrocardiogram data at 20:45 from the terminal device 1. Therefore, the controller 23 determines that the physiological information received in STEP02 does not include the backfill waveform (NO in STEP03), and ends the present processing.

In STEP04 of FIG. 3, the determination unit 231 determines whether the backfill waveform specified in STEP03 is a triangular waveform. That is, the determination unit 231 determines whether the complementary physiological information corresponding to the non-transmission time is authentic physiological information or pseudo physiological information. When the backfill waveform is not the triangular waveform (NO in STEP04), the determination unit 231 determines that the complementary physiological information corresponding to the non-transmission time is the authentic physiological information. In this case, the determination unit 231 determines that the non-transmission time is generated since the communication state between the terminal device 1 and the access point AP is the unconnected state, and the controller 23 ends the present processing based on the determination. On the other hand, when the backfill waveform is the triangular waveform (YES in STEP04), the determination unit 231 determines that the complementary physiological information corresponding to the non-transmission time is the pseudo physiological information. In this case, the determination unit 231 determines that the non-transmission time is generated since the power is not transmitted to the terminal device 1 and the terminal device 1 is in the inoperable state, and the controller 23 starts processing of STEP05 based on the determination.

As illustrated in FIG. 4B, in the present embodiment, the backfill waveform corresponding to the complementary physiological information is a triangular waveform (YES in STEP04), so that the determination unit 231 determines that the complementary physiological information corresponding to the non-transmission time is pseudo physiological information. As a result, the determination unit 231 determines that the non-transmission time is generated since the power is not transmitted to the terminal device 1 and the terminal device 1 is in the inoperable state, and the controller 23 starts processing of STEP05 based on the determination.

In STEP05 of FIG. 3, the determination unit 231 determines whether time corresponding to the triangular waveform is equal to or longer than predetermined time based on the length of the non-transmission time. When the non-transmission time is shorter than the predetermined time (NO in STEP05), the controller 23 ends the present processing. On the other hand, when the non-transmission time is equal to or longer than the predetermined time (YES in STEP05), the first determination information is generated by the generator 232, and the processing proceeds to STEP06.

As illustrated in FIG. 4B, in the present embodiment, a time point at which the terminal device 1 transmits the complementary physiological information to the information generation device 2 is 20:45, and a time point at which the terminal device 1 does not transmit the electrocardiogram data to the information generation device 2 is 20:32, so that the length of the non-transmission time (time corresponding to the triangular waveform) is 13 minutes. Therefore, the non-transmission time is 10 minutes or longer (YES in STEP05), so that the controller 23 starts processing of STEP06.

In STEP06 of FIG. 3, the determination unit 231 determines, by pattern-matching a waveform corresponding to the first physiological information and a waveform corresponding to the second physiological information, whether the first physiological information and the second physiological information is acquired from the subject P. When one of the first physiological information and the second physiological information is not the physiological information acquired from the subject P (NO in STEP06), the controller 23 ends the present processing. On the other hand, when both the first physiological information and the second physiological information is the physiological information acquired from the subject P (YES in STEP06), the processing proceeds to STEP07.

In the present embodiment, the first physiological information acquired before 20:31 on Feb. 7, 2020 and the second physiological information acquired from 20:45 is the electrocardiogram data of the subject P. Therefore, the determination unit 231 determines, by pattern-matching the waveform corresponding to the first physiological information and the waveform corresponding to the second physiological information, that both the first physiological information and the second physiological information is acquired from the subject P (YES in STEP06), and the controller 23 starts processing of STEP07.

In STEP07 of FIG. 3, the generator 232 generates first alert information based on the first determination information. At this time, the generator 232 generates information on a time point at which the first alert information is generated. The controller 23 specifies information on the subject P associated with identification information of the terminal device 1, information on the healthcare professional, information on the ward, or the like based on, for example, the identification information of the terminal device 1 and various pieces of table information stored in the memory 22. The information on the time point at which the first alert information is generated, the information on the subject P, or the like is associated with the first alert information generated in STEP07 and is transmitted to the memory 22. For example, when the first alert information is not generated since the time corresponding to the triangular waveform is shorter than the predetermined time (NO in STEP05), the generator 232 generates information on the time point at which the determination unit 231 determines that the time corresponding to the triangular waveform is shorter than the predetermined time. At this time, the controller 23 specifies information on the subject P associated with identification information of the terminal device 1, information on the healthcare professional, information on the ward, or the like based on, for example, the identification information of the terminal device 1 and various pieces of table information stored in the memory 22. The information on the time point at which the determination unit 231 determines that the time corresponding to the triangular waveform is shorter than the predetermined time, the information on the subject P, or the like is transmitted to the memory 22.

When the healthcare professional performs, on the operation unit 33 of the central monitor device 3, an operation for outputting a data set including the first alert information in a predetermined period and information on the subject P or the healthcare professional in the predetermined period after the first alert information is generated, a command signal for outputting the data set in the period is transmitted to the information generation device 2 from the central monitor device 3. The output unit 24 outputs the data set in the period based on the command signal, and outputs an output signal OS corresponding to the output data set to the central monitor device 3 (STEP08). As a result, a display screen based on the output signal OS is displayed on the display 32 of the central monitor device 3.

For example, when the healthcare professional performs, on the operation unit 33 of the central monitor device 3, an operation for outputting a data set for the last five days, the output unit 24 outputs the data set from Feb. 3, 2020 to Feb. 7, 2020, and outputs the output signal OS corresponding to the output data set to the central monitor device 3. The healthcare professional may figure out whether time from removing the battery B from the terminal device 1 to placing a new battery in the terminal device 1 is appropriate from Feb. 3, 2020 to Feb. 7, 2020 by viewing the display screen displayed on the display 32. For example, when the information on the healthcare professional is included in the output data set, a healthcare professional may figure out which healthcare professional has not appropriately replaced the battery B provided in the terminal device 1 by viewing the display screen displayed on the display 32.

When the remaining capacity of the battery B provided in the terminal device 1 is 0, the terminal device 1 is in an inoperable state. Accordingly, it is required to replace the battery as soon as possible. On the other hand, an emergency situation may suddenly occur before the battery B is removed from the terminal device 1 and then a new battery is placed. In this case, time from removing the battery B from the terminal device 1 to placing the new battery may be long. In the past, healthcare professionals had no choice but to actively consciously act so that the replacement time of the battery would not be long.

According to the above configuration, when non-transmission time occurs since power is not supplied to the terminal device 1, and the non-transmission time is equal to or longer than the predetermined time, the generator 232 generates the first alert information. For example, the number of times the first alert information is generated in a desired period is displayed on the display 32 of the central monitor device 3, and thereby, the healthcare professional may know, as numerical data, whether replacement of the battery B provided in the terminal device 1 in the desired period is appropriately performed. Namely, the healthcare professional may objectively figure out, by viewing the information displayed on the display 32, how much the battery B provided in the terminal device 1 can be appropriately replaced by himself or other healthcare professionals. In this manner, according to the information generation device 2, the healthcare professional may aware that the battery B provided in the terminal device 1 is appropriately replaced.

According to the above configuration, when the receiver 21 becomes unable to receive the authentic physiological information from the terminal device 1 and then becomes able to receive the physiological information from the terminal device 1, the receiver 21 receives the complementary physiological information corresponding to the non-transmission time. The determination unit 231 determines the complementary physiological information to be the authentic physiological information or the pseudo physiological information. For example, when the determination unit 231 determines that the complementary physiological information received by the receiver 21 is the pseudo physiological information, the determination unit 231 may determine that the receiver 21 cannot receive the physiological information from the terminal device 1 since the power is not supplied to the terminal device 1. Therefore, the healthcare professional may recognize, based on the first alert information generated by the information generation device 2, whether the non-transmission time is caused by, for example, radio wave disconnection or battery depletion.

According to the above configuration, when the first physiological information and the second physiological information are physiological information on the same subject P, the generator 232 generates the first alert information. Therefore, the generator 232 does not generate the first alert information, for example, when the non-transmission time is generated at the time of changing the subject associated with the terminal device 1. When the physiological information is continuously acquired from the same subject P, it is not preferable to generate the non-transmission time. The information generation device 2 generates the first alert information when the first physiological information and the second physiological information is the physiological information on the same subject P, so that it is possible to more accurately assist the healthcare professional to appropriately replace the battery B provided in the terminal device 1.

According to the above configuration, the first alert information generated by the generator 232 is associated with at least one of the information on the subject P, the information on the healthcare professional, the information on the ward, and the information on the time point at which the first alert information is generated, and is stored in the memory 22. Therefore, the healthcare professional can easily specify, based on the first alert information, for example, a healthcare professional who cannot appropriately replace the battery B provided in the terminal device 1, or a time zone at which it is difficult to appropriately replace the battery B provided in a ward or a terminal device.

According to the above configuration, the output unit 24 outputs the data set including the first alert information in the predetermined period, the information on the subject P in the predetermined period, or the like. Therefore, the healthcare professional can figure out, in a list, the healthcare professional who cannot appropriately replace the battery B provided in the terminal device, and the time zone at which it is difficult to appropriately replace the battery B provided in the ward or the terminal device, which are in a certain period.

Second Embodiment

Next, a second embodiment will be described with reference to FIG. 5. In the description of the second embodiment, the same parts as those in the first embodiment will be omitted. Also in the second embodiment, it is assumed that the physiological information illustrated in FIGS. 4A and 4B is acquired from the subject P. The second embodiment describes that the authentic physiological information is not transmitted to the information generation device 2 from the terminal device 1 at 20:32 on Feb. 7, 2020 because the remaining capacity of the battery B is 0. Namely, in the second embodiment, a battery depletion time point is 20:32 on Feb. 7, 2020.

In the second embodiment, when a remaining capacity of the battery B provided in the terminal device 1 is equal to or less than a predetermined value, the controller 12 generates battery depletion advanced notification information indicating that the remaining capacity of the battery B is equal to or less than the predetermined value. In the present embodiment, the predetermined value is described as one that is set to be 15% for convenience of explanation. In this case, when the remaining capacity of the battery B is 15% or less, the controller 12 generates the battery depletion advanced notification information. The generated battery depletion advanced notification information is transmitted to the information generation device 2 from the transmitter 13 via the access point AP and the network N, so that the receiver 21 receives the battery depletion advanced notification information from the terminal device 1 (STEP11).

When the receiver 21 receives the battery depletion advanced notification information, the determination unit 231 of the controller 23 determines a battery depletion time point of the battery B based on the received battery depletion advanced notification information (STEP12). For example, when the power of the battery B is consumed by 1% per minute and a time point at which the battery depletion advanced notification information is generated is 20:17 on Feb. 7, 2020, the determination unit 231 determines that a battery depletion time point is 20:32 on Feb. 7, 2020.

Figure 5:
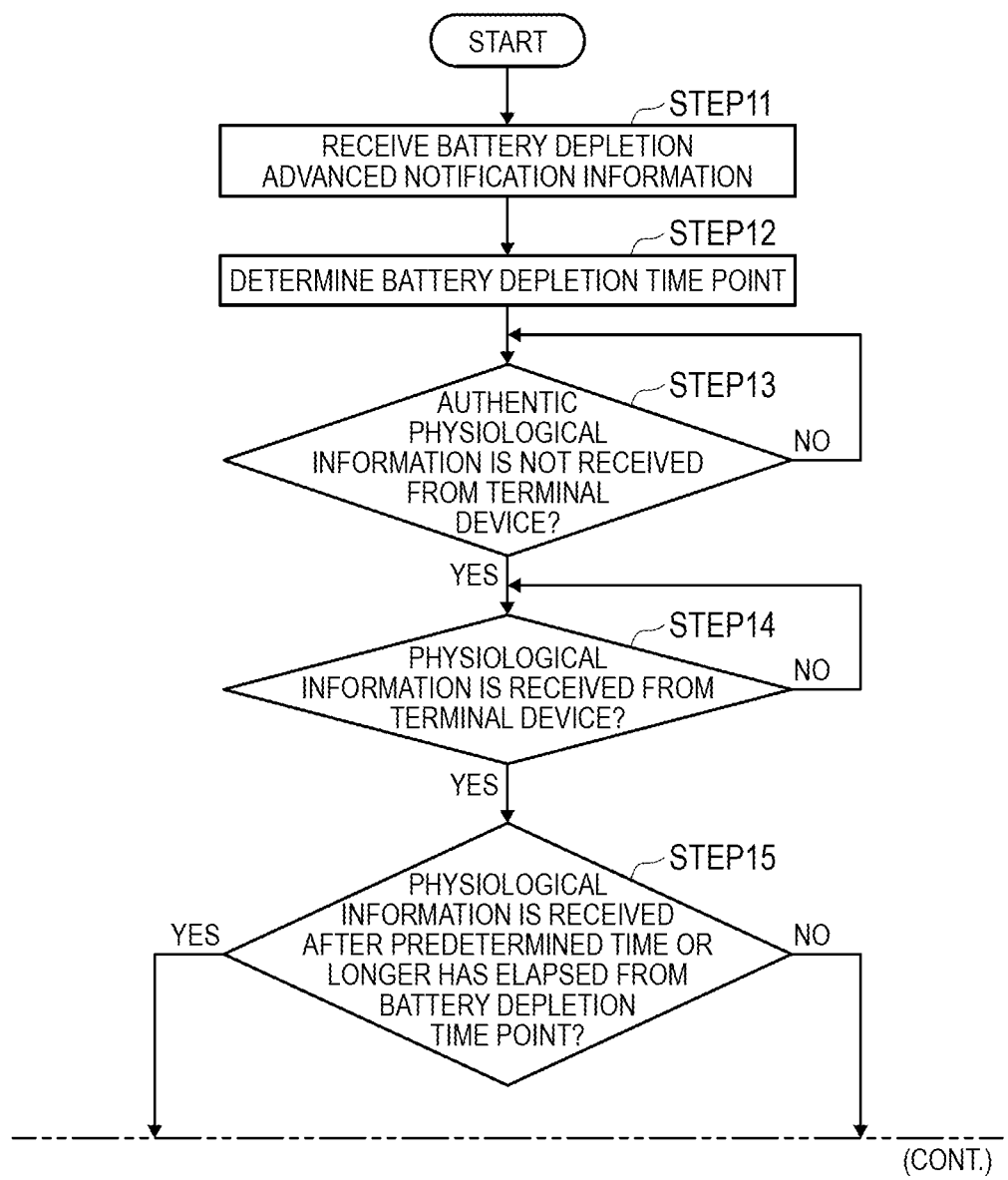
FIG. 5 is a flowchart according to a second embodiment.

STEPS 13 and 14 in FIG. 5 are the same as STEPS 01 and 02 in FIG. 3.

In STEP15, the determination unit 231 determines whether the receiver 21 receives the physiological information from the terminal device 1 after predetermined time or longer has elapsed from the battery depletion time point. In the present embodiment, the receiver 21 receives the physiological information from the terminal device 1 at a time point of 20:45 after the authentic physiological information is not received from the terminal device 1. Therefore, for example, when the predetermined time is 13 minutes, a time point (20:45) at which the physiological information is received elapses from the battery depletion time point (20:32) by 13 minutes (YES in STEP15), so that the processing proceeds to STEP16. In this case, the determination unit 231 generates second determination information. On the other hand, for example, when the predetermined time is 15 minutes, the time point (20:45) at which the physiological information is received does not elapse from the battery depletion time point (20:32) by 15 minutes (NO in STEP15), so that the processing proceeds to STEP22.

STEPS 16 to 19 in FIG. 5 are the same as STEPS 03 to 06 in FIG. 3.

In STEP20, the generator 232 generates first alert information based on first determination information, and generates second alert information based on second determination information. At this time, the generator 232 generates information on a time point at which the first alert information and the second alert information is generated. At this time, the controller 23 specifies, information on the subject P associated with identification information of the terminal device 1, information on the healthcare professional, information on the ward, or the like based on, for example, the identification information of the terminal device 1 and various pieces of table information stored in the memory 22. The information on the time point at which the first alert information and the second alert information is generated or the information on the subject P is associated with the first alert information and the second alert information generated in STEP20 and is transmitted to the memory 22. For example, when the first alert information and the second alert information is not generated since the time corresponding to the triangular waveform is shorter than the predetermined time (NO in STEP18), the generator 232 generates information on a time point at which the determination unit 231 determines that the time corresponding to the triangular waveform is shorter than the predetermined time. At this time, the controller 23 specifies information on the subject P associated with identification information of the terminal device 1, information on the healthcare professional, information on the ward, or the like based on, for example, the identification information of the terminal device 1 and various pieces of table information stored in the memory 22. The information on the time point at which the determination unit 231 determines that the time corresponding to the triangular waveform is shorter than the predetermined time, the information on the subject P, or the like is transmitted to the memory 22.

When the healthcare professional performs, on the operation unit 33 of the central monitor device 3, an operation for outputting a data set including the first alert information and the second alert information in a predetermined period and information on the subject P or the healthcare professional in the predetermined period after the first alert information and the second alert information is generated, an output signal OS corresponding to the data set in the period is output to the central monitor device 3 (STEP21). As a result, a display screen based on the output signal OS is displayed on the display 32 of the central monitor device 3.

For example, when the healthcare professional performs, on the operation unit 33 of the central monitor device 3, an operation for outputting a data set for the last five days, the output unit 24 outputs the data set from Feb. 3, 2020 to Feb. 7, 2020, and outputs the output signal OS corresponding to the output data set to the central monitor device 3. The healthcare professional can figure out, by viewing a display screen displayed on the display 32, from Feb. 3, 2020 to Feb. 7, 2020, whether the battery B is left for a long time after the remaining capacity of the battery B provided in the terminal device 1 is 0 and whether the time from removing the battery B from the terminal device 1 to placing a new battery in the terminal device 1 is appropriate. For example, when the information on the healthcare professional is included in the output data set, a healthcare professional may figure out whether the healthcare professional has appropriately replaced the battery B provided in the terminal device 1 by viewing the display screen displayed on the display 32.

STEPS 22 to 27 in FIG. 5 are the same as STEPS 03 to 08 in FIG. 3.

According to the above configuration, when the determination unit 231 determines that the receiver 21 does not receive the physiological information within the predetermined time from the battery depletion time point based on the battery depletion advanced notification information (an example of information on the remaining capacity of the battery) received from the terminal device 1, the generator 232 further generates the second alert information. Therefore, the healthcare professional figures out, for example, the number of times for which the time from the running out of the battery B of the terminal device 1 to placing the new battery into the terminal device 1 exceeds the predetermined time, by using the second alert information, so that the healthcare professional may know, as numerical data, whether the replacement of the battery B provided in the terminal device 1 is appropriately performed. As a result, the healthcare professional may aware that the battery B provided in the terminal device 1 is appropriately replaced.

The embodiments described above are intended to facilitate understanding of the presently disclosed subject matter, and are not intended to limit the presently disclosed subject matter. The presently disclosed subject matter can also be modified and improved without departing from the spirit thereof.

In the above embodiment, the authentic physiological information is the electrocardiogram data of the subject P, and the authentic physiological information may be physiological waveform on other pieces of physiological information such as pulse, electroencephalogram, non-invasive arterial oxygen saturation ($SpO_2$), body temperature, blood pressure, and respiratory rate.

In the first embodiment, STEP06 is executed, and STEP06 may not be executed. Namely, in the case of YES in STEP05, the first alert information may be generated without executing STEP06.

In the second embodiment, STEP 19 or STEP 25 may be executed, and STEP 19 or STEP 25 may not be executed. Namely, in the case of YES in STEP 18, the first alert information and the second alert information is generated without executing STEP 19. In the case of YES in STEP 24, the first alert information is generated without executing STEP 25.

In the above embodiment, the first alert information or the first alert information and the second alert information is presented to a healthcare professional by displaying a display screen based on the output signal OS on the display 32 of the central monitor device 3, but the presently disclosed subject matter is not limited to this example. For example, the first alert information or the first alert information and the second alert information may be presented to a healthcare professional by outputting a printed matter in which the information based on the output signal OS is displayed from a printer associated with the information generation device 2 or the central monitor device 3.

In the above embodiment, the operation unit 33 is provided in the central monitor device 3, and the operation unit may be provided in, for example, any one of the terminal device 1, the information generation device 2, and other external devices. For example, when the operation unit is provided in the information generation device 2, and a healthcare professional performs a predetermined operation on the operation unit provided in the information generation device 2, the operation unit generates a command signal for outputting a data set in a predetermined period, and transmits the command signal to the controller 23.

In STEP07 of the first embodiment or STEP 26 of the second embodiment, the generator 232 generates the information on the time point at which the first alert information is generated, and only the first alert information may be generated. In STEP07 of the first embodiment or STEP 26 of the second embodiment, the controller 23 may specify the information on the subject P associated with the identification information of the terminal device 1, the information on the healthcare professional, the information on the ward, and the like based on the identification information of the terminal device 1 and various pieces of table information stored in the memory 22.

In the second embodiment, the generator 232 generates the information on the time point, at which the first alert information and the second alert information is generated, in STEP20, and only the first alert information and the second alert information may be generated. In STEP20, the controller 23 may specify the information on the subject P associated with the identification information of the terminal device 1, the information on the healthcare professional, the information on the ward, and the like based on the identification information of the terminal device 1 and various pieces of table information stored in the memory 22.

In the above embodiment, the controller 23 of the information generation device 2 specifies the subject P associated with the identification information of the terminal device 1 or the like based on the identification information of the terminal device 1 received from the terminal device 1 and various pieces of table information stored in the memory 22, but the presently disclosed subject matter is not limited to this example. For example, the terminal device 1 may transmit the information on the subject P associated with the terminal device 1, the information on the healthcare professional, the information on the ward, or the like to the information generation device 2. In this case, the controller 23 of the information generation device 2 associates the first alert information or the first alert information and the second alert information, which is generated by the generator 232, with the information on the subject P received from the terminal device 1. The associated information is transmitted to the memory 22.

In the second embodiment, the determination unit 231 of the information generation device 2 determines the battery depletion time point of the battery B based on the battery depletion advanced notification information, but the presently disclosed subject matter is not limited to this example. For example, the controller 12 of the terminal device 1 may determine the battery depletion time point of the battery B based on the remaining capacity of the battery B and the power consumption per minute of the battery 13. In this case, the controller 12 generates the battery depletion time point information based on the determination result and transmits the battery depletion time point information to the information generation device 2.

In the above embodiment, the information generation device 2 is described as a device different from the central monitor device 3, and for example, the information generation device 2 may have a function corresponding to the display 32, the operation unit 33, and the controller 34 of the central monitor device 3. In this case, the medical system 100 does not include the central monitor device 3.

The presently disclosed subject matter can provide an information generation device, a computer program, and a non-transitory computer-readable medium, which can help a healthcare professional appropriately replace a battery provided in a terminal device.

The invention claimed is:

1. An information generation device comprising:
    a receiver configured to receive physiological information of a subject, from a terminal device configured to operate by power of a battery, and continuously acquire and transmit the physiological information;
    a determination unit configured to determine whether non-transmission time, during which the terminal device is not capable of transmitting the physiological information to the receiver since the power is not supplied to the terminal device, is equal to or longer than a first predetermined time; and
    a generator configured to generate first alert information indicating that the non-transmission time is equal to or longer than the first predetermined time, when the determination unit determines that the non-transmission time is equal to or longer than the first predetermined time.

2. The information generation device according to claim 1, wherein when the receiver receives complementary physiological information corresponding to the non-transmission time from the terminal device, the determination unit is configured to determine whether the complementary physiological information is physiological information acquired from the subject or pseudo physiological information indicating that physiological information is not acquired from the subject.

3. The information generation device according to claim 1, wherein:
    the determination unit further is configured to determine whether first physiological information acquired immediately before the non-transmission time and second physiological information acquired immediately after the non-transmission time are physiological information on the same subject, and
    the generator is configured to generate the first alert information when the determination unit determines that the first physiological information and the second physiological information are physiological information on the same subject.

4. The information generation device according to claim 1, wherein the generated first alert information is associated with at least one of information on the subject, information on a healthcare professional, information on a ward, and information on a time point at which the first alert information is generated, and is stored.

5. The information generation device according to claim 4, further comprising an output unit configured to output a data set that includes the first alert information in a predetermined period, and at least one of the information on the subject, the information on the healthcare professional, the information on the ward, and the information on the time point, which are in the predetermined period.

6. The information generation device according to claim 1, wherein:
    the receiver is configured to receive information on a remaining capacity of the battery from the terminal device,
    the determination unit is configured to determine, based on information on the remaining capacity of the battery, whether the receiver receives the physiological information within a second predetermined time from a battery depletion time point that is a time point at which the remaining capacity of the battery is 0, and
    when the determination unit determines that the receiver does not receive the physiological information within the second predetermined time from the battery depletion time point, the generator is further configured to generate second alert information.

7. An information generation method, comprising:
    receiving physiological information of a subject, from a terminal device configured to operate by power of a battery, and continuously acquire and transmit the physiological information;
    determining whether non-transmission time, during which the terminal device is not capable of transmitting the physiological information since the power is not supplied to the terminal device, is equal to or longer than a predetermined time; and
    generating first alert information indicating that the non-transmission time is equal to or longer than the predetermined time, when it is determined that the non-transmission time is equal to or longer than the predetermined time.

8. A non-transitory computer-readable medium storing a program for causing a computer to execute the information generation method according to claim 7 is recorded.

* * * * *